_United States Patent_ [19]

Bellamy et al.

[11] Patent Number: 5,451,609

[45] Date of Patent: Sep. 19, 1995

[54] TREATMENT OF IMPOTENCE

[75] Inventors: François Bellamy, Saulon la Rue; Philippe Reginault, Fontaine lès Dijon; Bernard Rasquin, Nogent sur Marne, all of France

[73] Assignee: Institut De Recherches Chimiques et al, France

[21] Appl. No.: 281,425

[22] Filed: Jul. 27, 1994

[51] Int. Cl.$^6$ .......................................... A61K 31/135
[52] U.S. Cl. .................................... 514/651
[58] Field of Search ........................................ 514/651

[56] References Cited

U.S. PATENT DOCUMENTS 4,336,396  6/1982  Giordano et al. ................ 560/20
5,182,270  1/1993  Musson et al. .................. 514/58

OTHER PUBLICATIONS

The Merck Index, 11th Edition, 1989, p. 991, (monograph No. 6204).

Vidal 1993, 69th Edition, Editions du Vidal, Paris 1993, p. 689, (entries "ICAVEX 10 mg" and ICAVEX 20 mg.
P. Costa et al, "Efficiency and Side Effects of Intracavernous Injections of Moxisylyte in Impotent Patients: A Dose-Finding Study Versus Placebo", J. Urol., 149, pp. 301–305, 1993.
Christian G. Stief et al, "Erectile Dysfunction: Progress in Basic Physiology, Diagnosis and Treatment", European Urology, vol. 1, No. 2, pp. 10–15, 1992.

*Primary Examiner*—José C. Dees
*Assistant Examiner*—Barbara S. Frazier
*Attorney, Agent, or Firm*—Ostrolenk, Faber, Gerb & Soffen

[57] ABSTRACT

This invention is concerned with a novel anti-impotence composition and a novel method for the treatment of impotence, whereby deacetyl moxisylyte or one of its non-toxic salts is administered in a ready to use aqueous solution by injection per intracavernosal route, as a drug inducing a substantially rigid penile erection.

15 Claims, No Drawings

TREATMENT OF IMPOTENCE

FIELD OF THE INVENTION

Impotence is one of the major erectile dysfunctions which prevent males from normal sexual intercourse. This invention relates to the treatment of impotence, and to be precise is concerned with (i) a novel therapeutical composition and (ii) a novel method for the treatment of impotence involving both the use of deacetyl moxisylyte or a non-toxic salt thereof as a drug inducing a substantially rigid penile erection by intracavernosal injection.

PRIOR ART

Moxisylyte is a reference α-adrenergic blocking agent, which is known in particular from The Merck Index, 11th edition, 1989, page 991 (monograph number: 6204).

Moxisylyte is now known from the Vidal 1993, 69th edition, Editions du Vidal, Paris 1993, page 689 (entries "ICAVEX 10 mg" and "ICAVEX 20 mg"), and the article by P. COSTA et al. J. Urol., 149, page 301–305, (1993), to be useful in the pharmacologically induced penile erection. Moxisylyte, also called thymoxamine, corresponds to the systematic nomenclature of 4-[2-(dimethylamino)ethoxy]-2-methyl-5-(1-methylethyl)-phenol acetate and has the following structure:

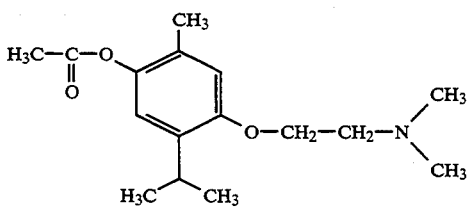

After parenteral administration, in particular per intracavernosal route as disclosed in the above cited Vidal 1993, moxisylyte is deacetylated by plasmatic esterases, and at the plasma level are found (a) deacetyl moxisylyte (in short: DAM), which corresponds to the systematic nomenclature of 4-[2-(dimethylamino)ethoxy]-2-methyl-5-(1-methylethyl)phenol and has the following structure:

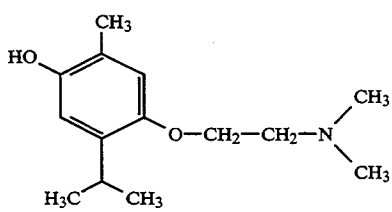

as a major or main metabolite (in both the free and conjugated forms), and (b) N-monodemethyl deacetyl moxisylyte (in short MDAM), which corresponds to the systematic nomenclature of 4-[2-(methylamino)ethoxy]-2-methyl-5-(1-methylethyl)phenol and has the following structure:

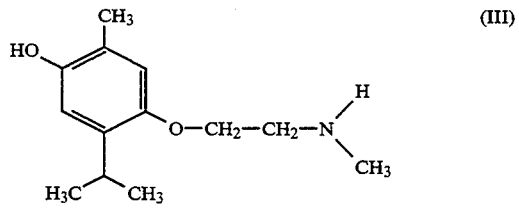

as a minor or secondary metabolite (in the conjugated form).

Aqueous solutions of moxisylyte are not stable at room temperature, the moxisylyte, which comprises in its structure an acetate moiety, being hydrolyzed by bases to give a phenol compound, and by acids to give a quinone compound after oxidation.

Consequently, it is not possible to commercialize moxisylyte in the form of a ready to use injectable aqueous solution.

As commercialized in France (see the above cited Vidal 1993), the moxisylyte.HCl compound marketed as ICAVEX 10 mg and ICAVEX 20 mg specialties, is in the form of a lyophilized product; the specialty comprises a syringe containing the lyophilized moxisylyte.HCl powder, an ampoule containing water as a solvent and a needle destined to equip said syringe; the user fills the syringe with the solvent in order to dissolve the lyophilized moxisylyte.HCl powder before injecting the resulting solution per intracavernosal route.

One will easily understand that, for a drug to be administered by injection in the penis per intracavernosal route in order to combat impotence, a situation where the psychological state of the patient is of great importance, it is necessary to provide a product as simple to use as possible and not involving a series of manipulations which can put the patient in an unfavourable situation for a good treatment effect.

U.S. Pat. No. 5,182,270 (to Donald G. MUSSON et al.) provides a stable moxisylyte solution, in which dimethyl-beta-cyclodextrin intervenes as a stabilizing agent for preventing the moxisylyte (used here as an α-adrenergic blocking agent) from hydrolysis. When said dimethyl-beta-cyclodextrin is used as a stabilizing agent, a pH 5 solution containing 1 mg/ml of moxisylyte is stable at 45° C. for 3 months.

However such a dimethyl-beta-cyclodextrin/moxisylyte formulation has the drawback of being very expensive because the price of dimethyl-beta-cyclodextrin is high. Moreover administering such dimethyl-beta-cyclodextrin/moxisylyte formulation per intracavernosal route would mean injecting a stabilizing product, which has an unknown long term toxicity and which does not provide per se any therapeutical advantage.

SUMMARY OF THE INVENTION

It has been surprisingly found now that deacetyl moxisylyte, a product known per se, in particular as a metabolite of moxisylyte, is (i) stable in aqueous solution unlike moxisylyte, and (ii) active as a drug inducing a substantially rigid penile erection.

Consequently, provided here is a novel therapeutical composition and a novel method of treatment of impotence using deacetyl moxisylyte or one of its nontoxic salts as a substantially rigid penile erection inducing agent to be administered per i.p. route, and to be precise by intracavernosal injection.

SUBJECT OF THE INVENTION

According to a first aspect of the invention an anti-impotence composition is provided, said composition comprising in a ready to use aqueous solution a therapeutically effective amount of a compound inducing a substantially rigid penile erection which is selected from the group consisting of
(i) deacetyl moxisylyte, and
(ii) non-toxic salts thereof,
said aqueous solution being administered by injection in the penis per intracavernosal route.

According to a second aspect of the invention, a method for the treatment of impotence is provided, said method comprising administering, by injection in the penis per intracavernosal route, to a patient in need of such a treatment, an aqueous solution containing a therapeutically effective amount of a compound selected from the group consisting of
(i) deacetyl moxisylyte, and
(ii) non-toxic salts thereof,
as a substantially rigid penile erection inducing agent.

DETAILED DISCLOSURE OF THE INVENTION

In the expression a "substantially rigid penile erection", the term "substantially" relates to the penile rigidity. The rigidity which is looked for is at least the one which is necessary for or compatible with vaginal admission. Consequently the expression "substantially rigid" includes within its scope both the "rigid" and "partially rigid" erections allowing a normal sexual intercourse.

The anti-impotence composition according to the invention presents the advantage to be simple and economical to use. The active ingredient, which induces the penile erection, namely deacetyl moxisylyte (DAM) of the formula II or one of its non-toxic salts, is dissolved in an aqueous solution for i.p. injection according to a classical well known technique.

Among the non-toxic salts of deacetyl moxisylyte are included here the physiologically acceptable acid addition salts, in particular those obtained by reacting the deacetyl moxisylyte free base with an inorganic or organic acid, such as hydrochloric acid or tartaric acid.

The anti-impotence composition according to the invention, which is made from pure (i.e. distilled, bidistilled or preferably deionized) water and the rigid penile erection inducing agent, can contain further excipient products. Advantageously, said excipient products can comprise:
(a) a buffer material,
(b) an antioxidant material, and/or
(c) an organic co-solvent.

According to the invention, in cases where it is necessary to adjust the pH of the DAM-containing aqueous solution, it is recommended to use a solution buffered at pH 5-7 with potassium dihydrogen phosphate ($KH_2PO_4$), sodium dihydrogen phosphate ($NaH_2PO_4$), disodium hydrogen phosphate ($Na_2HPO_4$), sodium chloride (NaCl), sodium hydroxide (NaOH) or mixtures thereof; in those cases, the buffer material (here $KH_2PO_4$, $NaH_2PO_4$, $Na_2HPO_4$, NaCl, NaOH or a mixture thereof) will be at a concentration of from 2 to 15 g/l (i.e. 0.2–1.5% p/v) and preferably at a concentration of from 8 to 12 g/l (i.e. 0.8–1.2% p/v).

According to the invention, in cases where it is advantageous to add an antioxidant material into the DAM-containing aqueous solution, it is preferred to use a DAM-containing solution which comprises from 0.001 to 0.01 g/l (i.e. 0.01–0.1% p/v) of an antioxidant agent such as for instance
$K_2SO_3$ or (preferably) $Na_2SO_3$,
$KHSO_3$ or (preferably) $NaHSO_3$,
$K_2S_2O_5$ or (preferably) $Na_2S_2O_5$, or
ascorbic acid or a physiologically acceptable salt thereof.

The addition of an antioxidant material can be either replaced by or associated with a preparation technique wherein the aqueous composition according to the invention is prepared from its components under an inert atmosphere (in particular under nitrogen or argon), whereby the solvent (or solvents) used is (are) previously degassed.

According to the invention, it is also possible to add into the DAM-containing aqueous solution a supplemental solvent which is used here as a co-solvent. That co-solvent is in a general manner an alcohol or polyol compound. In the case where such a co-solvent is present, it is preferred to use ethanol, propylene glycol, glycerol or a polyethylene glycol, (such as $PEG_{300}$ or $PEG_{400}$) in a proportion up to 50% by volume with respect to the total volume of the anti-impotence composition of the invention.

First, it was determined that DAM, the active ingredient inducing a substantially rigid penile erection, is effectively hydrosoluble in the form of its hydrochloride salt. It was observed that deacetyl moxisylyte hydrochloride (DAM.HCl) is soluble up to the concentration of 10% p/v, which is the upper therapeutically acceptable concentration, in pure (i.e. distilled, bidistilled or preferably deionized) water and in aqueous solutions buffered at pH 5–7.

Secondly, the stability of the DAM.HCl-containing aqueous solution according to the invention was evaluated in order to appreciate whether or not said solution can be considered as a ready for use one. To that aim several solutions were tested, in the presence or the absence of an antioxidant material, at different pH values and at different temperatures.

It was observed in particular that solutions containing 1% p/v of deacetyl moxisylyte hydrochloride and no antioxidant and kept at pH 5, 6 and 7, were stable for 15 days at 25° C. and for 90 minutes at 121° C.

All the tested solutions, which contained no antioxidant and were kept for 15 days at 95° C., presented a slight coloration. Identical solutions, in which $Na_2SO_3$ used as an antioxidant was added in order to reach a sodium sulfite concentration of 0.1% p/v in said solutions, did not give any coloration and were stable for 15 days at 95° C.

The solutions containing no antioxidant which were treated at pH 5, 6 or 7, for 15 days at 25° C., for 15 days at 95° C. or for 90 minutes at 121° C., were assayed by gas chromatography for quantifying their impurities. It was observed that the pH 5 solution kept for 15 days at 95° C. presented an impurity rate of 1.6% p/v, whereas the remaining solutions presented an impurity rate lower than or equal to 0.4% p/v.

The DAM-containing aqueous solution can be sterilized according to a well known classical technique without degradation of DAM. Autoclave sterilization for 15 minutes at 121° C. and sterilizing filtration are here the preferred sterilization techniques.

BEST MODE

The best mode for carrying out the invention consists in administering in the penis by intracavernosal injection, to a patient in need of an treatment to combat impotence, a single dose of from 0.5 to 5 ml of an aqueous solution containing from 0.5 to 10% p/v (preferably from 1 to 3.5% p/v) of deacetyl moxisylyte or one of its non-toxic acid addition salts. The recommended posology is two injections per week.

Further characteristics and advantages of the invention will be understood more clearly from the following description of preparatory Examples, pharmacological experiments and clinical assays, which in no way imply a limitation and are given by way of illustration.

EXAMPLES 1-6

Compositions according to the invention were prepared according to the formulations presented in Table I hereinafter. Syringes, destined for injecting (per a single injection) a volume of from 0.5 to 5 ml of liquid, were filled with these compositions so as to be ready to use and contained each from 1 to 3.5% p/v of deacetyl moxisylyte hydrochloride (DAM.HCl).

In Table I, the amounts of water are expressed in ml (namely: bidistilled or deionized water up to 100 ml) and those of the remaining components in grams (g).

CLINICAL ASSAYS 26 patients complaining of erectile dysfunctions (of psychologic or organic origin), who presented either a penile tumescence or a poorly rigid penile erection but were not able to achieve or sustain a sufficiently rigid penile erection for sexual intercourse when subjected to an audiovisual sexual stimulation test [such a test is mentioned in Christian G. STIEF et al., European Urology 1 (No 2), pages 10-15, (1992)], were double-blind injected, per intracavernosal route, with 1 ml of either the composition of example 1 (16 patients) or a control solution having a formulation identical to the one of Ex 1 but without deacetyl moxisylyte hydrochloride (10 patients). The penile rigidity and erection duration were observed after the single injection of the 1 ml solution (Ex 1 or control). The results thus obtained are summed up in Table II hereinafter.

The data of Table II show that:

(1) the audiovisual sexual stimulation test (AVSST), generally used as a selection test to determine whether or not an impotent patient can be treated per intracavernosal route with a drug improving erectile rigidity, intervened here as a supplemental control test in order to appreciate the evolution of both the erection rigidity and erection duration induced by a drug solution to be tested;

(2) the 16 patients who were injected with the Ex 1 solution presented an increase in both the erection rigidity and erection duration with respect to the control patients and the AVSST results; to be precise, those 16 patients had all after the intracavernosal injection a substantially rigid penile erection and an erection duration (30-60 minutes; average: 43 minutes) compatible with a normal sexual intercourse, whereas the 9 out of 10 patients, who were injected with the control solution, were unable to perform sexual intercourse (there was one case of "placebo" effect among the control patients); and, (3) among the 16 patients who received the injection of the Ex 1 solution, DAM.HCl was well tolerated, no undesirable side effect, such as priapism (rigid penile erection for 3 hours or more), was observed.

PHARMACOLOGICAL EXPERIMENTS (1) Assays on male dogs

The aqueous solution of Ex 6, as obtained or previously diluted with bidistilled or deionized water up to ½ or 1/5, was injected twice a week for 3 months under a volume of 0.5 ml per intracavernosal route to adult male dogs. [Since adult male dogs are in a general manner sexually stimulated only in the presence of a bitch in heat, they can be considered as "impotent" in the absence of a bitch in heat].

During the 3-month experiment, the adult male dogs presented each a rigid penile erection compatible with mating after every injection. Unlike moxisylyte, no canine priapism side effect was observed with the Ex 6 solution and dilutions thereof containing each deacetyl moxisylyte hydrochloride as the active ingredient. Those DAM.HCl-containing solutions were well tolerated by the animals.

(2) Assays on anaesthetized male rabbits

Adult male White New Zealand rabbits weighing each about 3.5 kg were anaesthetized with urethan (1.50 to 1.75 g/kg) injected into a marginal ear vein. Each animal was put in a dorsal decubitus position; to prevent hypothermia, animal body temperature was maintained at 38.5° C. by means of an electrically heated blanket and the whole animal body was covered with an insulating survival blanket.

After tracheotomy, each trachea was cannulated. The systemic arterial blood pressure was measured via a catheter in the carotid artery with a GOULD P23 XL pressure transducer connected to a GOULD ES 1000 POLYGRAPH recorder. Via a midline laparotomy the bladder was exteriorized. The two branches of the pelvic nerve were identified and one of them was placed on bipolar electrodes. The penis of each animal was denuded of skin to the crura. A 21-gauge butterfly needle was placed into a *corpus cavernosum* and was connected to a GOULD P23 XL pressure transducer for recording the intracavernous pressure (ICP). For evaluating the reactivity of each animal, the pelvic nerve was stimulated with square wave pulses (6 milliseconds at 16 Hz with a 15 V stimulus during 1 minute from a NARCO SI 10 stimulator). When the ICP was returned to baseline (i.e. about 1 hour after having placed said butterfly needle in position), a 26-gauge needle was placed into the other corpus cavernosum for administering (after a time lapse of 20 minutes) each drug to be tested. Batches of 5 animals each per drug to be tested received by injection per intracavernous route 3.5 mg of moxisylyte hydrochloride or deacetyl moxisylyte hydrochloride in saline solution (bidistilled water containing 9 g/l of NaCl) under a volume of 0.17 ml, the control batch (10 animals) receiving only 0.17 ml of said saline solution. The 3.5 mg/0.17 ml dose solution of each drug to be tested was prepared extemporeanously from lyophilized moxisylyte hydrochloride powder or crystallized deacetyl moxisylyte hydrochloride powder, before injection.

The results which were obtained are given in Table III hereinafter. The data of Table III show that (i) deacetyl moxisylyte hydrochloride and moxisylyte hydrochloride exhibit similar effects when both the increase in the intracavernous pressure (ICP) and the increase in the duration of penile tumescence/erection (DTE) are concerned, and (ii) deacetyl moxisylyte hydrochloride induces a decrease (−7%) in the blood pressure (BP) which is lower than the one induced by moxisylyte hydrochloride (−14%), a −7% decrease in BP being pharmacologically acceptable whereas a −14% decrease in BP is generally considered as a drawback.

All those assays do point out that, unlike moxisylyte, deacetyl moxisylyte (as well as its non-toxic acid addition salts)
(i) is stable in aqueous solution,
(ii) does not need to be lyophilized before being used in solution, and
(iii) does not exhibit the drawback to induce an important decrease in the blood pressure, when administered by injection per intracavernosal route (see Table III).

TABLE I

| Formulations of examples 1-6 | | | | | | |
|---|---|---|---|---|---|---|
| | Ex 1 | Ex 2 | Ex 3 | Ex 4 | Ex 5 | Ex 6 |
| DAM.HCl | 1 g | 1 g | 2 g | 3.5 g | 1 g | 1 g |
| NaCl | 0.2 g | 0.2 g | — | — | — | — |
| $KH_2PO_4$ | 0.8 g | 0.4 g | 0.4 g | 0.4 g | 0.8 g | 0.8 g |
| $NaH_2PO_4$ | 0.1 g | 0.6 g | 0.6 g | 0.6 g | 0.1 g | 0.1 g |
| $Na_2SO_3$ | 0.01 g | — | — | — | — | — |
| Ascorbic acid | — | 0.05 g | 0.05 g | — | — | — |
| Propylene glycol | — | — | — | 30 g | — | — |
| Ethanol | — | — | — | — | 20 g | — |
| $PEG_{300}$ | — | — | — | — | — | 40 g |
| $H_2O$ up to | 100 ml | 100 ml | 100 ml | 100 ml | 100 ml | 100 ml |

TABLE II

| CLINICAL ASSAYS | | |
|---|---|---|
| | Control | Ex 1 |
| patients: | | |
| number | 10 | 16 |
| ages (years) | 39-72 | 40-76 |
| audiovisual sexual stimulation | | |
| number of IRE (a) | 10 | 16 |
| duration of IRE (a) | | |
| average (minutes) | 10.8 | 10.7 |
| range (minutes) | 8-15 | 8-15 |
| intracavernosal injection | | |
| injected volume (ml) | 1 | 1 |
| DAM.HCl amount (% p/v) | — | 1 |
| number of IRE (a) | 9 | — |
| duration of IRE (a) | | |
| average (minutes) | 4.7 | — |
| range (minutes) | 0-8 | — |
| number of SRE (b) | 1 (c) | 16 |
| duration of SRE (b) | | |
| average (minutes) | 20 | 43 |
| range (minutes) | — | 30-60 |

Notes:
(a) IRE = insufficiently rigid erection (i.e. a penile tumescence or a poor penile rigidity incompatible with vaginal intromission)
(b) SRE: substantially rigid erection (i.e. a penile rigidity compatible with vaginal intromission)
(c) a "placebo" effect for one patient.

TABLE III

| ASSAYS ON ANAESTHETIZED MALE RABBITS | | |
|---|---|---|
| | Moxisylyte.HCl | DAM.HCl |
| dose | 3.5 mg/0.17 ml | 3.5 mg/0.17 ml |
| number of animals | 5 | 5 |
| ICP increase (mm Hg) (a) | 29.4 ± 9.4 | 30.1 ± 2.8 |
| DTE (minutes) | 15 to 60 | 10 to 60 |

TABLE III-continued

| ASSAYS ON ANAESTHETIZED MALE RABBITS | | |
|---|---|---|
| | Moxisylyte.HCl | DAM.HCl |
| BP variation | −14% | −7% |

Notes:
ICP: intracavernous pressure
DTE: duration of the penile tumescence/erection
BP: blood pressure
(a): 1 mm Hg represents 133.32 Pa

What is claimed is:

1. An anti-impotence composition comprising in a ready to use aqueous solution a therapeutically effective amount of a compound inducing a substantially rigid penile erection which is selected from the group consisting of
(i) deacetyl moxisylyte, and
(ii) non-toxic salts thereof,
said aqueous solution being administered by injection in the penis per intracavernosal route.

2. An anti-impotence composition according to claim 1, containing from 0.5 to 10% p/v of deacetyl moxisylyte or one of its non-toxic acid addition salts.

3. An anti-impotence composition according to claim 1, having a pH between 5 and 7.

4. An anti-impotence composition according to claim 1, said composition further comprising from 0.01 to 0.1% p/v of an antioxidant material.

5. An anti-impotence composition according to claim 1, said composition further comprising an organic co-solvent representing up to 50% by volume with respect to the total volume of the composition.

6. An anti-impotence composition according to claim 5, wherein said co-solvent is selected from the group consisting of ethanol, propylene glycol, glycerol and polyethylene glycol.

7. A method of treatment of impotence, said method comprising administering, by injection in the penis per intracavernosal route, to a patient in need of such a treatment, an aqueous solution containing a therapeutically effective amount of a compound selected from the group consisting of
(i) deacetyl moxisylyte, and
(ii) non-toxic salts thereof,
as a substantially rigid penile erection inducing agent, 8. A method according to claim 7 wherein the concentration of deacetyl moxisylyte or one of its non-toxic acid addition salts is between 0.5 and 10% p/v.

9. An anti-impotence composition according to claim 2, having a pH bettween 5 and 7.

10. An anti-impotence composition according to claim 9, said composition further comprising from 0.01 to 0.1% p/v of an antioxidant material.

11. An anti-impotence composition according to claim 10, said composition further comprising an organic co-solvent representing up to 50% by volume with respect to the total volume of the composition.

12. An anti-impotence composition according to claim 11, wherein said co-solvent is selected from the group consisting of ethanol, propylene glycol, glycerol and polyethylene glycol.

13. An anti-impotence composition according to claim 12, wherein said compound is deacetyl moxisylyte hydrochloride.

14. An anti-impotence composition according to claim 2, said composition further comprising an organic cosolvent representing up to 50% by volume with respect to the total volume of the composition.

15. An anti-impotence composition according to claim 1, wherein said compound is deacetyl moxisylyte hydrochloride.

* * * * *